US00PP15521P2

(12) United States Plant Patent
Brown

(10) Patent No.: US PP15,521 P2
(45) Date of Patent: Feb. 1, 2005

(54) ***DIASCIA* PLANT NAMED 'CODITER'**

(50) Latin Name: *Diascia×hybrida*
Varietal Denomination: Coditer

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 2 days.

(21) Appl. No.: 10/818,492

(22) Filed: Apr. 5, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Diascia* plant named 'Coditer', characterized by its upright and somewhat outwardly spreading plant habit; freely branching habit; freely flowering habit; light red-colored flowers; and good temperature tolerance.

1 Drawing Sheet

Botanical classification/cultivar designation: *Diascia×hybrida* cultivar Coditer.

BACKGROUND OF THE INVENTION

The present Invention relates to a new and distinct cultivar of *Diascia* plant, botanically known as *Diascia×hybrida,* and hereinafter referred to by the cultivar name Coditer.

The new *Diascia* is a product of a planned breeding program conducted by the Inventor in Cobbitty, New South Wales, Australia. The objective of the breeding program is to create new compact *Diascias* with numerous flowers and attractive flower coloration.

The new *Diascia* originated from a cross-pollination made by the Inventor in the spring of 2000 of a proprietary *Diascia×hybrida* selection identified as code number X99.55.5, not patented, as the female, or seed parent, with a proprietary *Diascia×hydrida* selection identified as code number X99.62.2, not patented, as the male, or pollen parent. The new *Diascia* was selected as a single plant from the resulting progeny of the cross-pollination by the Inventor in September, 2001, in an controlled environment in Cobbitty, New South Wales, Australia.

Asexual reproduction of the new cultivar by terminal cuttings in a controlled environment in Cobbitty, New South Wales, Australia since September, 2001 has shown that the unique features of this new *Diascia* are stable and reproduced true to type in successive generations.

SUMMARY OF THE INVENTION

Plants of the cultivar Coditer have not been observed under all possible environmental conditions. The phenotype may vary somewhat with variations in environment such as temperature and light intensity without, however, any variance in genotype.

The following traits have been repeatedly observed and are determined to be the unique characteristics of 'Coditer'. These characteristics in combination distinguish 'Coditer' as a new and distinct cultivar of *Diascia:*

1. Upright and somewhat outwardly spreading plant habit.
2. Freely branching habit.

3. Freely flowering habit.
4. Light red-colored flowers.
5. Good temperature tolerance.

Plants of the new *Diascia* differ from plants of the female parent selection primarily in flower color as plants of the female parent selection have light orange-colored flowers. Plants of the new *Diascia* are more compact and flower earlier than plants of the male parent selection.

Plants of the new *Diascia* can be compared to plants of the cultivar Copiap, disclosed in U.S. Plant Pat. No. 11,488. In side-by-side comparisons conducted in Cobbitty, New South Wales, Australia, plants of the new *Diascia* differed from plants of the cultivar Copiap in the following characteristics:

1. Plants of the new *Diascia* were more freely flowering than plants of the cultivar Copiap.
2. Plants of the new *Diascia* and the cultivar Copiap differed in flower color as plants of the cultivar Copiap had soft orange-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Diascia.*

The photograph at the top of the sheet comprises a side perspective view of a typical flowering plant of 'Coditer' grown in a container.

The photograph at the bottom of the sheet comprises a close-up view of typical flowers of 'Coditer'.

DETAILED BOTANICAL DESCRIPTION

The aforementioned photographs and following observations and measurements describe plants grown in Encinitas, Calif., in an outdoor nursery during the winter and spring with day temperatures averaging 24° C., night temperatures averaging 12° C., and light levels about 6,000 foot candles.

Plants were grown for about 16 weeks with three plants per one-gallon container; plants were pinched one time.

Color references are made to The Royal Horticultural Society Colour Chart, 1995 Edition, except where general terms of ordinary dictionary significance are used.

Botanical classification: *Diascia×hybrida* cultivar Coditer.

Parentage:

*Female parent.*—Proprietary *Diascia×hybrida* selection identified as X99.55.5, not patented.

*Male parent.*—Proprietary *Diascia×hybrida* selection identified as X99.62.2, not patented.

Propagation:

*Type cutting.*—Terminal vegetative cuttings.

*Time to initiate roots, summer and winter.*—About one week at 20° C.

*Time to produce a rooted young plant, summer and winter.*—About three weeks at 20° C.

*Root description.*—Fine, fibrous; white in color.

*Rooting habit.*—Freely branching; dense.

Plant description:

*Form.*—Upright and compact plant habit. Freely branching with lateral branches potentially forming at every node. Vigorous growth habit.

*Plant height.*—About 30 cm.

*Plant diameter, single plant.*—About 23 cm.

*Lateral branches.*—Appearance: Thin, wiry; upright. Length: About 30 cm. Diameter: About 1.5 mm. Internode length: About 1.9 cm. Texture: Smooth, glabrous. Color: 144A overlain 185B.

*Foliage description.*—Arrangement: Opposite; simple. Length: About 2.8 cm. Width: About 1.5 cm. Shape: Deltoid. Apex: Broadly acute. Base: Truncate. Margin: Slightly serrate. Texture, upper and lower surfaces: Smooth, glabrous. Venation pattern: Pinnate. Color: Developing foliage, upper surface: 146A. Developing foliage, lower surface: 146B. Fully expanded foliage, upper surface: 147A. Fully expanded foliage, lower surface: 147B. Venation, upper and lower surfaces: 147B. Petiole length: About 6 mm. Petiole diameter: About 2 mm. Petiole color: 144A.

Flower description:

*Flower type and habit.*—Solitary zygomorphic flowers arranged on terminal racemes. Five modified petals fused at base: two upper (banner) petals, two lateral petals, and one larger lower lip petal. Flowers not persistent. Flowers face mostly outwardly.

*Quantity.*—Freely flowering; typically about 14 to 18 buds and flowers per lateral branch.

*Natural flowering season.*—Plants typically flower during the spring in the Northern Hemisphere; flowering continuous during this period.

*Flower longevity on the plant.*—About four days.

*Fragrance.*—Not detected.

*Inflorescence size.*—Length: About 8.5 cm. Width: About 4.5 cm.

*Flower size.*—Length: About 2.3 cm. Width: About 2.2 cm. Depth: About 1.5 cm.

*Flower buds (showing color).*—Length: About 4 mm. Diameter: About 5 mm. Shape: Ovoid. Color: 50B.

*Petals.*—Quantity/arrangement: Five modified petals fused at base: two upper (banner) petals, two lateral petals, and one larger lower lip petal. Base of banner petals with concave yellow eyespots; lower surfaces of lateral petals modified into nectar spurs; and lower lip petal convex forming a roughly horizontal insect landing platform. Length: Banner petals: About 7 mm. Lateral petals: About 8 mm. Lower lip petal: About 1 cm. Width: Banner petals: About 6 mm. Lateral petals: About 8 mm. Lower lip petal: About 1.2 cm. Lateral petal spur: Length: About 8 mm. Diameter, at petal attachment: About 2 mm. Shape, all petals: Roughly spatulate. Apex, all petals: Rounded. Margin, all petals: Entire. Texture, all petals, upper and lower surfaces: Smooth, velvety. Color, all petals: When opening, upper surface: 50A. When opening, lower surface: 50B. Fully opened, upper surface: 50A; towards base, 46A. Fully opened, lower surface: 50B. Nectar spurs: 51A. Eyespot on banner petals: 12A.

*Sepals.*—Arrangement/appearance: Single whorl of five sepals fused at base; star-shaped. Length: About 4 mm. Width: About 2 mm. Shape: Elliptic. Apex: Acute. Margin: Entire. Texture, upper and lower surfaces: Smooth, glabrous. Color, upper and lower surfaces: 144A.

*Peduncles.*—Length: About 3.75 cm. Width: About 1 mm. Angle: Upright to about 45° from vertical. Strength: Moderately strong. Texture: Smooth, glabrous. Color: 144A.

*Pedicels.*—Length: About 1.4 cm. Width: Less than 1 mm. Angle: About 45° from the peduncle. Strength: Moderately strong; slender. Texture: Smooth, glabrous. Color: 144A.

*Reproductive organs.*—Stamens: Quantity per flower: Four. Anther shape: Ovoid. Anther length: Less than 1 mm. Anther color: 11A. Pollen amount: Scarce. Pollen color: 11A. Pistils: Quantity per flower: One. Pistil length: About 4 mm. Style length: About 2 mm. Style color: 145B. Stigma shape: Rounded. Stigma color: 145B. Ovary color: 145A.

*Fruit/seed.*—Fruit and seed production has not been observed.

Disease/pest resistance: Plants of the new *Diascia* have not been noted to be resistant to pathogens or pests common to *Diascia*.

Temperature tolerance: Plants of the new *Diascia* have been observed to tolerate temperatures from 0 to 35° C.

It is claimed:

1. A new and distinct cultivar of *Diascia* plant named 'Coditer', as illustrated and described.

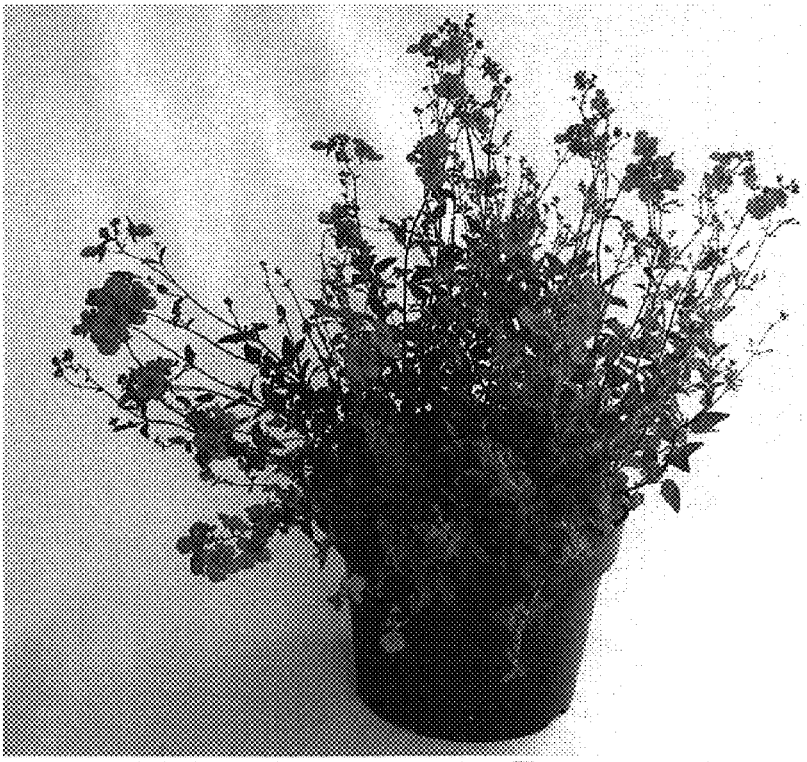
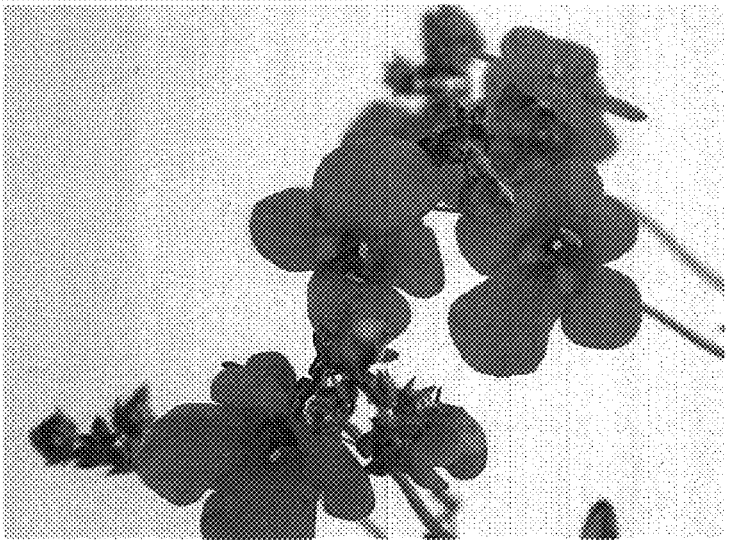

* * * * *